United States Patent
Kanan et al.

(10) Patent No.: US 10,160,740 B2
(45) Date of Patent: Dec. 25, 2018

(54) CARBONATE-PROMOTED CARBOXYLATION REACTIONS FOR THE SYNTHESIS OF VALUABLE ORGANIC COMPOUNDS

(71) Applicant: The Board of Trustees of the Leland Stanford Junior University, Palo Alto, CA (US)

(72) Inventors: Matthew W. Kanan, Palo Alto, CA (US); Aanindeeta Banerjee, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/558,528

(22) PCT Filed: Mar. 17, 2016

(86) PCT No.: PCT/US2016/022969
§ 371 (c)(1),
(2) Date: Sep. 14, 2017

(87) PCT Pub. No.: WO2016/153937
PCT Pub. Date: Sep. 29, 2016

(65) Prior Publication Data
US 2018/0244639 A1      Aug. 30, 2018

Related U.S. Application Data

(60) Provisional application No. 62/136,288, filed on Mar. 20, 2015.

(51) Int. Cl.
*C07D 307/68* (2006.01)
*C07C 51/02* (2006.01)
*C07C 51/15* (2006.01)

(52) U.S. Cl.
CPC ............ *C07D 307/68* (2013.01); *C07C 51/02* (2013.01); *C07C 51/15* (2013.01)

(58) Field of Classification Search
CPC ........ C07D 307/68; C07C 51/02; C07C 51/15
See application file for complete search history.

(56) References Cited

U.S. PATENT DOCUMENTS

| | | | |
|---|---|---|---|
| 2,900,386 | A | 8/1959 | Raecke et al. |
| 2,948,750 | A | 8/1960 | Blaser et al. |
| 3,359,310 | A | 12/1967 | Raecke et al. |
| 2012/0059176 | A1 | 3/2012 | Walker et al. |
| 2013/0345448 | A1 | 12/2013 | Shaikh et al. |
| 2014/0364633 | A1 | 12/2014 | Janka et al. |

FOREIGN PATENT DOCUMENTS

| | | |
|---|---|---|
| DE | 60023335 | 4/2006 |
| WO | 01/016077 | 3/2001 |
| WO | 2010/070593 | 6/2010 |
| WO | 2014/099438 | 6/2014 |

OTHER PUBLICATIONS

International Search Report from International Application No. PCT/US16/22969 dated Jun. 3, 2016.
Written Opinion from International Application No. PCT/US16/22969 dated Jun. 3, 2016.
Kudo, Kiyoshi, "Carboxylation of Cesium, 2-Naphthoate in the Alkali Metal Molten Salts of Carbonate and Formate with CO2 under High Pressure", Institute for Chemical Research, Kyoto University, vol. 38, No. 1, pp. 40-47, Jun. 22, 1994.
Kudo, Kiyoshi, "Synthesis of oxalate from carbon monoxide and carbon dioxide in the presence of caesium carbonate", Institute for Chemical Research, Kyoto University, J. Chem. Soc., Perkin Trans. 2, pp. 679-682, 1997.
German Office Action from German Application No. 11 2016 001 317.5 dated Feb. 20, 2018.
Brian D. Andresen "Synthesis of Sodium Formate C and Oxalic Acid", Department of Pharmaceutical Chemistry, J. Org. Chem, vol. 42, No. 16, 1977, p. 2790.

*Primary Examiner* — Timothy R Rozof
(74) *Attorney, Agent, or Firm* — Beyer Law Group LLP

(57) ABSTRACT

A method for synthesizing furan-2,5-dicarboxylate (FDCA$^{2-}$) is provided. Furan-2-carboxylic acid is provided. A CO$_3^{2-}$ salt is provided to form a mixture, which converts the furan-2-carboxylic acid to furan-2-carboxylate. CO$_2$ gas is provided to a mixture of the furan-2-caboxylic acid and CO$_3^{2-}$ salt. The mixture is heated to a temperature to at least partially melt the furan-2-caboxylate.

6 Claims, 3 Drawing Sheets

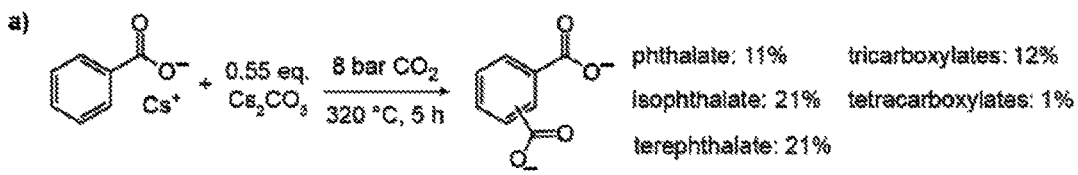
FIG. 3a
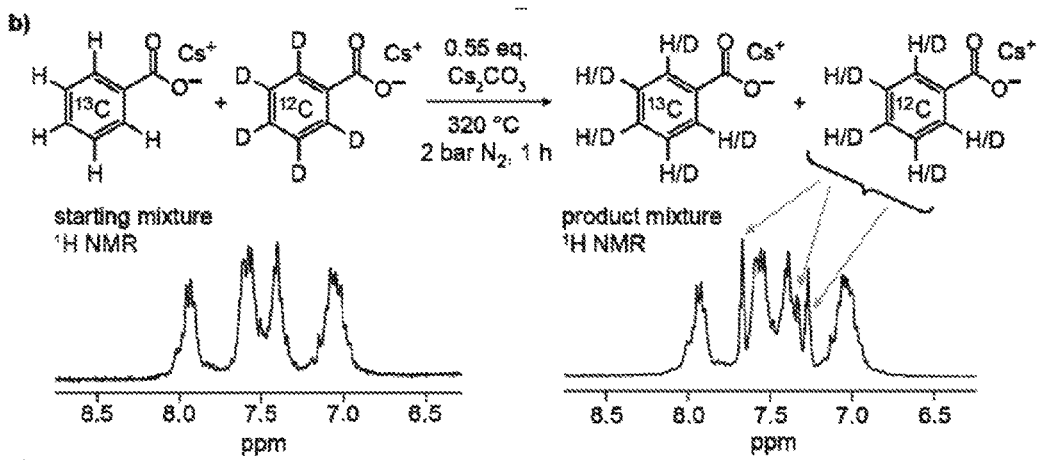
FIG. 3b
FIG. 3c
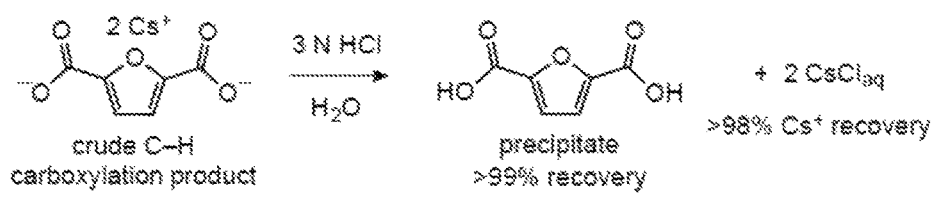
FIG. 4

CARBONATE-PROMOTED CARBOXYLATION REACTIONS FOR THE SYNTHESIS OF VALUABLE ORGANIC COMPOUNDS

CROSS REFERENCE TO RELATED APPLICATIONS

This application claims priority under 35 U.S.C. § 119 from U.S. Provisional Patent Application No. 62/136,288, filed Mar. 20, 2015, entitled Carbonate-Promoted Carboxylation Reactions for the Synthesis of Valuable Organic Compounds, which is incorporated herein by reference for all purposes.

BACKGROUND

This disclosure relates generally to the reduction of $CO_2$. More specifically, this disclosure relates to the formation of carbon based chemicals and carbon based fuels using $CO_2$.

SUMMARY

In accordance with this disclosure, a method for synthesizing furan-2,5-dicarboxylate ($FDCA^{2-}$) is provided. Furan-2-carboxylic acid is provided. A $CO_3^{2-}$ salt is provided to form a mixture, which converts the furan-2-carboxylic acid to furan-2-carboxylate. $CO_2$ gas is provided to the mixture. The mixture is heated to a temperature to at least partially melt the furan-2-caboxylate.

In another manifestation, a method for forming aromatic tricarboxylate salts is provided. An aromatic dicarboxylic acid is provided. A $CO_3^{2-}$ salt is provided to form a mixture, which converts the aromatic dicarboxylic acid to aromatic dicarboxylate. The mixture is heated under $CO_2$ gas to a temperature sufficient to at least partially melt the aromatic dicarboxylate.

In another manifestation, method for forming aryl acetate and aryl malonate salts is provided. A substrate with an aromatic ring substituted with an alkyl group and a carboxylic acid is provided. $CO_3^{2-}$ salt is provided to form a mixture, which converts the carboxylic acid to a carboxylate. The mixture is heated under $CO_2$ gas to a temperature sufficient to at least partially melt the carboxylate.

In another manifestation, a method for forming carboxylate salts is provided. An organic molecule without a carboxylate is provided. $CO_3^{2-}$ salt is provided. A molten salt is provided. $CO_2$ gas is provided to a mixture of the organic molecule, $CO_3^{2-}$ salt, and molten salt. The mixture is heated to a temperature to maintain the molten salt.

In another manifestation, a method for forming organic compounds with one or more carbon-carbon bonds is provided. $H_2$ is provided. A $CO_3^{2-}$ salt is provided. $H_2O$ is provided. $CO_2$ is provided. A mixture of the $H_2$ $CO_3^{2-}$ salt, $H_2O$, and $CO_2$ is heated to a reaction temperature at an elevated pressure.

The invention and objects and features thereof will be more readily apparent from the following detailed description and appended claims when taken with the drawings.

BRIEF DESCRIPTION OF THE DRAWINGS

FIG. 3a schematically illustrates the carboxylation of cesium benzoate.

FIG. 3b schematically illustrates $CO_3^{2-}$-catalyzed H/D isotope exchange between differentially labeled benzoates.

FIG. 3c schematically illustrates carboxylation of benzene in the presence or absence of $Cs^+$ isobutyrate.

FIG. 4 schematically illustrates the isolation of FDCA by protonation with strong acid.

DETAILED DESCRIPTION OF ILLUSTRATED EMBODIMENTS

A major impediment to synthesizing compounds from $CO_2$ is the difficulty of forming carbon-carbon (C—C) bonds efficiently. $CO_2$ reacts readily with carbon-centered nucleophiles, but generating these intermediates has previously required high-energy reagents (e.g. highly reducing metals or strong organic bases), carbon-heteroatom bonds, and/or relatively acidic C—H bonds. These requirements negate the environmental benefit of using $CO_2$ as a substrate and limit the chemistry to low-volume targets. This specification shows that intermediate temperature (200° C.-350° C.) molten salts containing alkali cations (e.g. $Cs^+$ or $K^+$) enable carbonate ($CO_3^{2-}$) to deprotonate very weakly acidic C—H bonds (pKa>40), generating carbon-centered nucleophiles that react with $CO_2$ to form carboxylates (C—$CO_2^-$).

Figure 1A:
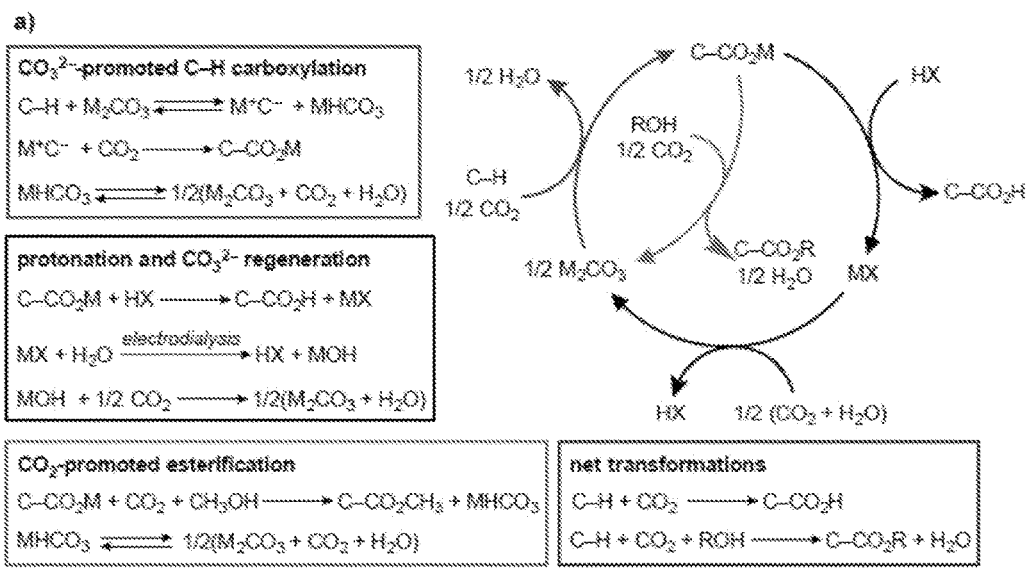
FIG. 1a is a schematic illustration of a $CO_3^{2-}$-promoted C—H carboxylation reaction.

To form C—C bonds to $CO_2$ without using high-energy reagents or specialized substrates, we envisioned a $CO_3^{2-}$-promoted C—H carboxylation reaction, wherein $CO_3^{2-}$ reversibly deprotonates a C—H bond to generate $HCO_3^-$ and a carbon-centered nucleophile that reacts with $CO_2$ to form C—$CO_2$, as shown in FIG. 1a. $HCO_3^-$ decomposition results in a net consumption of one-half equivalents of $CO_3^{2-}$ and $CO_2$ per C—$CO_2^-$ produced. The cycle could be closed by protonating C—$CO_2^-$ with strong acid and using electrodialysis to regenerate the acid and base, effecting a net transformation of C—H and $CO_2$ into C—$CO_2H$ without using any other stoichiometric reagents. Alternatively, $CO_2$-promoted esterification could be used to convert the carboxylate into an ester (C—$CO_2R$) and regenerate $CO_3^{2-}$ directly. Previously, researchers have used $Cs_2CO_3$ to promote C—H carboxylation in organic solvents. However, this approach can only be used to carboxylate relatively acidic C—H bonds such as alkynyl C—H bonds (Dingyi et al. *Green Chem.* 13, 1275-1279 (2011)), the alpha C—H bond in butenoate (Kudo et al. *J. Jpn. Petrol. Inst.* 38, 48-51 (1995)), and heteroaryl C—H bonds with pKa up to 27 (Vechorkin et al. *Org. Lett.* 12, 3567-3569 (2010)). This restriction severely limits the scope of molecules that can be carboxylated. Utilizing $CO_3^{2-}$-promoted C—H carboxylation for commodity synthesis requires deprotonating C—H bonds that are considerably less acidic.

A method reported by Raecke (U.S. Pat. No. 3,359,310) described the synthesis of potassium malonate by heating potassium acetate and potassium carbonate under high $CO_2$ pressure (10-2000 atm) at 200-450° C., but this method is limited to the synthesis of malonate. Raecke does not describe a general method for carboxylating C—H bonds in molecules unrelated to acetate. Another report by Kudo et al (*J. Jpn. Petrol. Inst.* 38, 40-47 (1995)) described the synthesis of aromatic dicarboxylic acid salts and tricarboxylic acid salts by combining cesium salts of aromatic carboxylic acids, cesium formate, and cesium carbonate under 400 atm of $CO_2$ and heating to 380° C. The use of very high $CO_2$ pressures makes the chemistry impractical. Kudo's conditions are intended to promote a reaction between $CO_2$ and an aromatic ring directly without first deprotonating a C—H bond on the substrate. This approach necessitates the very high $CO_2$ pressures. The following examples illustrate the generality and utility of $CO_3^{2-}$-promoted C—H carboxylation as depicted in FIG. 1a.

Figure 1B:
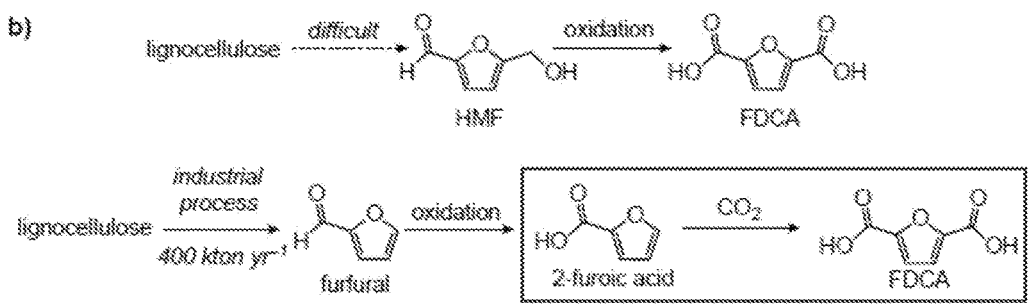
FIG. 1b is a schematic illustration of synthesis of FDCA from inedible biomass.

In one embodiment, $CO_3^{2-}$-promoted C—H carboxylation followed by protonation is used to convert 2-furoic acid into furan-2,5-dicarboxylic acid (FDCA). FDCA is a highly desirable bio-based feedstock with numerous applications including the synthesis of polyethylene furandicarboxylate (PEF), which is a potential large-scale substitute for petroleum-derived polyethylene terephthalate (PET). In particular, PEF has been reported to have superior physical properties to PET (Burgess, et al. *Macromolecules*, 47, 1383-1391 (2014)), a commodity polymer produced on a scale of many megatons per year (Mton $yr^{-1}$). A longstanding goal of renewable plastic synthesis is a scalable synthesis of FDCA from inedible biomass (lignocellulose), as shown in FIG. 1b. Current approaches to FDCA synthesis use dehydration processes to convert hexose sugars into hydroxymethyl furfural (HMF), which is then oxidized to form FDCA. Recent work has significantly improved the efficiency of converting fructose to HMF. However, producing FDCA on a scale commensurate with terephthalic acid and achieving maximal reduction in $CO_2$ emissions will require using lignocellulose as the feedstock. Converting lignocellulose into HMF is very challenging because the hexoses are incorporated into intractable cellulose fibers. An economical, large-scale lignocellulose-to-HMF process has not been demonstrated. (Sheldon *Green Chem.* 16, 950-963 (2014)).

In contrast to fructose, the conversion of lignocellulose to furfural has been performed industrially on a ~400 kton $yr^{-1}$ scale for decades (Lange et al. *ChemSusChem* 5, 150-166 (2012)). Furthermore, several methods are available for oxidizing furfural to 2-furoic acid (Hoydonckx et al. *Ullmann's Encyclopedia of Industrial Chemistry*, 16, 285-313 (2007)); (Van Haveren et al. WO 2013/096998 A1)). At present, however, the available methods for converting 2-furoic acid into FDCA are inefficient, unselective, and consume stoichiometric amounts of energy-intensive reagents (Thiyagaraj an et al. *RSC Adv.*, 3, 15678-15686 (2013)). $CO_3^{2-}$-promoted C—H carboxylation could be used to convert 2-furoic acid into FDCA and thereby open a new route to PEF utilizing a lignocellulose-derived monomer that is already produced industrially.

Figure 2A:
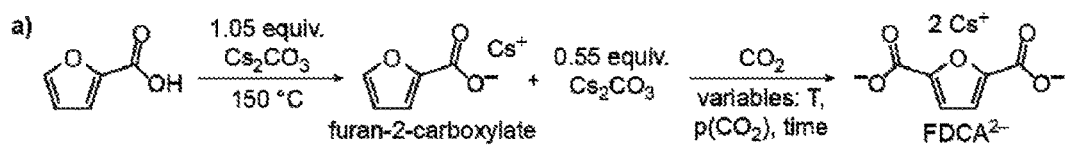
FIG. 2a is a schematic illustration of the conversion of furan-2-carboxylate into furan-2,5-dicarboxylate.

The $CO_3^{2-}$-promoted C—H carboxylation reaction required for FDCA synthesis is the conversion of furan-2-carboxylate into furan-2,5-dicarboxylate ($FDCA^{2-}$), as shown in FIG. 2a. Assuming it is similar to an un-substituted furan, the pKa of the C—H at the 5-position of furan-2-carboxylate is ~35. Deprotonation of this C—H has previously required lithium diisopropylamide or n-butyllithium. We hypothesized that $CO_3^{2-}$ would deprotonate furan-2-carboxylate if the reaction were performed in a molten salt with a high concentration of alkali cations to stabilize the conjugate base by ion pairing. To test this hypothesis, we attempted C—H carboxylation with mixtures consisting of an alkali metal salt of furan-2-carboxylate and an alkali metal carbonate. With these components, the reaction was found to proceed efficiently when $Cs^+$ salts were used, as shown in FIG. 2a and Extended Data Table 1. When 1 mmol of cesium furan-2-carboxylate and 0.55 mmol $Cs_2CO_3$ were heated at 260° C. under a $CO_2$ flow of 40 mL $min^{-1}$ in a tube furnace, $FDCA^{2-}$ was formed in 76% yield after 12 h, as shown in Entry 2 of Extended Data Table 1. The mass balance was composed of unreacted starting material and decomposition products including acetate. Reactions performed in a Parr reactor showed improved yields and less decomposition. In 1 mmol-scale reactions at 200° C. under 8 bar $CO_2$, $FDCA^{2-}$ was formed in a 77% yield after 2 h and 89% after 5 h, with only 5% decomposition products, as shown in Entries 5 and 6 of Extended Data Table 1. In 10 mmol-scale reactions under similar conditions, $FDCA^{2-}$ was formed in a 78% yield after 5 h and 81% yield after 10 h, as shown in Entries 8 and 9 of Extended Data Table 1. Further increasing the reaction time did not significantly increase the $FDCA^{2-}$ yield, while increasing the temperature diminished the yield because of increased decomposition. Increasing the $CO_2$ pressure slowed the reaction by sequestering $CO_3^{2-}$ in the form of $HCO_3^-$. Finally, a 100 mmol-scale reaction was performed under ~1 bar $CO_2$ in a rotating round-bottom flask in a 260° C. bath. After 48 h, $FDCA^{2-}$ was formed in a 71% yield, as shown in Entry 12 of Extended Data Table 1. The scaling behavior suggests that the reaction takes place at the molten salt-$CO_2$ interface. The reaction slows and the yield decreases somewhat as the scale is increased because the surface area-to-volume ratio decreases. Improved yields and rates are anticipated with reactors that disperse the salt more effectively.

| Extended Data Table 1 | | | | | | | | |
|---|---|---|---|---|---|---|---|---|
| Ent | Scale mmol | T ° C. | p($CO_2$) | Time h | $FDCA^{2-}$ | Start mat. | acetate | mal. | other |
| 1 | 1 | 260 | flowing | 6 | 57% | 26% | 4% | 4% | 9% |
| 2 | 1 | 260 | flowing | 12 | 76% | 8% | 4% | 4% | 8% |
| 3 | 1 | 260 | flowing | 20 | 76% | 8% | 5% | 3% | 8% |
| 4 | 1 | 270 | flowing | 4 | 66% | 10% | 7% | 8% | 9% |
| 5 | 1 | 200 | 8 bar | 2 | 77% | 18% | 2% | 1% | 2% |
| 6 | 1 | 200 | 8 bar | 5 | 89% | 6% | 3% | 2% | — |
| 7 | 1 | 200 | 8 bar | 7 | 89% | 4% | 2% | 1% | 4% |
| 8 | 10 | 195 | 8 bar | 5 | 78% | 11% | 4% | 1% | 6% |
| 9 | 10 | 195 | 8 bar | 10 | 81% | 8% | 4% | 1% | 6% |
| 10 | 10 | 205 | 8 bar | 2 | 71% | 7% | 9% | 3% | 10% |
| 11 | 10 | 215 | 8 bar | 2 | 69% | 2% | 14% | 5% | 10% |
| 12 | 100 | 260 | 1 bar | 48 | 71% | 3% | 11% | 2% | 1% |

Figure 2B:
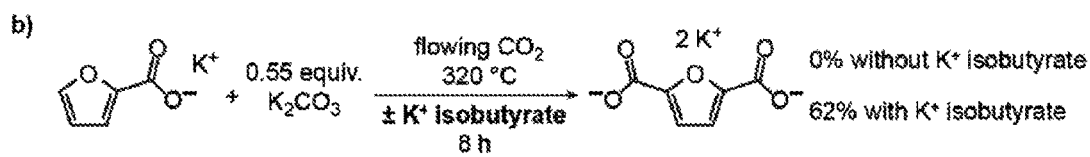
FIG. 2b is a schematic illustration of the conversion of furan-2-carboxylate into furan-2,5-dicarboxylate using potassium ($K^+$) salts.

Carboxylation using salts with cations other than $Cs^+$ can be achieved by incorporating another carboxylate salt or using cation mixtures. For example, heating $K^+$ furan-2-carboxylate with 0.5 equivalents of $K_2CO_3$ and 1 equivalent of $K^+$ isobutyrate at 320° C. under 40 mL $min^{-1}$ $CO_2$ resulted in 62% potassium $FDCA^{2-}$, as shown in FIG. 2b. Similar results were obtained with $K^+$ acetate as an additive. Thus, C—H carboxylation does not require $Cs^+$ per se, but $Cs^+$ salts typically have lower melting points.

Figure 2C:
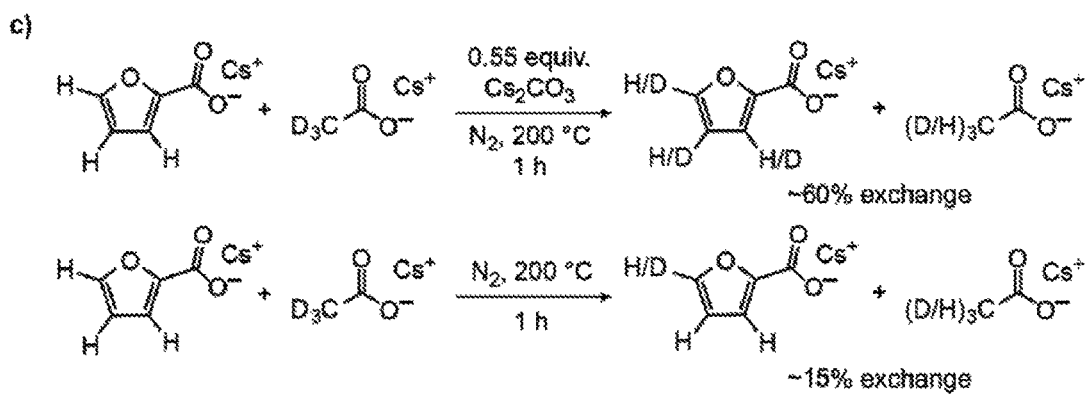
FIG. 2c schematically illustrates H/D isotopic exchange between furan-2-carboxylate and cesium acetate-d3.

While the carboxylation results are consistent with the mechanistic scheme in FIG. 1a, there are other possible mechanisms that do not involve a carbanion intermediate. To probe the acid-base properties of furan-2-carboxylate independently, an isotope exchange experiment was performed between furan-2-carboxylate and acetate. (The pKa of acetate is >33). A mixture of 1 mmol cesium furan-2-carboxylate, 1 mmol $CD_3CO_2Cs$, and 1.1 mmol $Cs_2CO_3$ was heated under $N_2$ in the Parr reactor to 200° C. for 1 h. $^1H$, $^2H$, $^{13}C$ NMR and high-resolution mass spectrometry of the crude product mixture showed H/D scrambling between acetate and the 5 position of furan-2-carboxylate and, to a lesser extent, the 3 and 4 positions. The H content remaining in furan-2-carboxylate indicated that the exchange was ~60% complete (FIG. 2c). When a 1:1 mixture of cesium furan-2-carboxylate and $CD_3CO_2Cs$ was heated in the absence of $Cs_2CO_3$ at 200° C., ~15% H/D exchange was observed, with nearly all of the exchange occurring at the 5 position (FIG. 2c). Thus, at 200° C. in a molten salt, a carboxylate is able to deprotonate the C5 position of furan-2-carboxylate, and $CO_3^{2-}$ is able to deprotonate all positions. The selectivity seen in the carboxylation reaction suggests a greater abundance of the carbanion that leads to $FDCA^{2-}$.

Additional substrates were evaluated to gain further insight into the $CO_3^{2-}$-promoted C—H carboxylation reaction. Heating the $Cs^+$ salt of thiophene-2-carboxylate with 0.55 equivalents of $Cs_2CO_3$ under flowing $CO_2$ at 325° C. resulted in 71% formation of thiophene-2,5-dicarboxylate after 4 h. This substrate required a significantly higher temperature than furan-2-carboxylate in order to form a semi-molten solution. To see if C—H carboxylation is possible for significantly weaker acids, we evaluated the reactivity of benzoate. Remarkably, heating $Cs^+$ benzoate with 0.55 equivalents of $Cs_2CO_3$ to 320° C. under 8 bar $CO_2$ resulted in a combined yield of 66% for a mixture of phthalates and tri- and tetracarboxylates (FIG. 3a). The ability of $CO_3^{2-}$ to deprotonate the C—H bonds of a phenyl ring was tested independently by heating a mixture of $^{12}C_6D_5CO_2Cs$, $^{13}C_6H_5CO_2Cs$, and 0.55 equivalents of $Cs_2CO_3$ to 320° C. under $N_2$ for 30 min. $^1H$ NMR analysis of the products revealed H/D scrambling at all positions on the benzoate ring, as shown in FIG. 3b. No H/D exchange was observed in the absence of $Cs_2CO_3$.

The results with benzoate suggest that benzene would undergo C—H carboxylation if exposed to $CO_3^{2-}$ in a molten salt. Heating $Cs_2CO_3$ under benzene and $CO_2$ at the temperatures up to 380° C. resulted in no reaction. The lack of reactivity can be attributed to the fact that $Cs_2CO_3$ does not melt. To provide a molten component, reactions were performed in the presence of $Cs^+$ isobutyrate. Heating 1.5 mmol $Cs_2CO_3$ and 1 mmol $Cs^+$ isobutyrate to 340-380° C. under 31 bar $CO_2$ and 42 bar benzene resulted in the formation of benzoate, phthalates, and benzene tricarboxylates, as shown in FIG. 3c. The amount of benzene carboxylation products corresponded to 12% of the $Cs_2CO_3$ at 350° C., and 19% at 360° C. In addition to benzene carboxylation, isobutyrate carboxylation to dimethyl malonate and decomposition to formate and acetate also occurred under these conditions. Extended Data Table 2 shows the results from the variation of various parameters. The carboxylation of benzene is more challenging than benzoate because there is a larger entropic penalty and the solubility of benzene in the carboxylate salt is likely to be very low. Nevertheless, these results demonstrate that $CO_3^{2-}$-promoted hydrocarbon carboxylation is possible.

Extended Data Table 2

| Ent | Time h | T ° C. | p($C_6H_6$) bar | p($CO_2$) bar | $CO_3^{2-}$ Conv. | A | B | C | D | E |
|---|---|---|---|---|---|---|---|---|---|---|
| 1 | 10 | 340 | 13 | 31 | 5% | 2 | 14 | 14 | 205 | 17 |
| 2 | 9 | 340 | 42 | 31 | 9% | 42 | 29 | 11 | 238 | 24 |
| 3 | 2 | 350 | 42 | 31 | 2% | 19 | 3 | 1 | 27 | 9 |
| 4 | 8 | 350 | 42 | 31 | 12% | 46 | 41 | 17 | 148 | 28 |
| 5 | 8 | 360 | 45 | 32 | 19% | 39 | 69 | 35 | 306 | 42 |
| 6 | 1 | 380 | 42 | 33 | 9% | 30 | 36 | 13 | 192 | 146 |

A is μmoles of benzonate. B is μmoles of phthalates. C is μmoles of benzene tri+tetracarboxylates. D is μmoles acetate+carboxylation products. E is μmoles formate. D and E correspond to isobutyrate decomposition products.

Scalable $CO_3^{2-}$-promoted C—H carboxylation requires facile product isolation and highly efficient recovery of the alkali cation. To illustrate the ease of product isolation in the case of FDCA synthesis, treatment of crude cesium $FDCA^{2-}$ from a C—H carboxylation reaction with 3 N HCl affords immediate precipitation of FDCA, leaving CsCl in the aqueous solution with >99% $Cs^+$ recovery, as shown in FIG. 4. To regenerate the $CO_3^{2-}$ necessary for C—H carboxylation, bipolar membrane electrodialysis could be used to convert CsCl into HCl and CsOH solutions and the CsOH could be combined with pure $CO_2$, ambient air, or flue gas to form $Cs_2CO_3$. HCl is recycled for the protonation step, while CsOH is reacted with 2-furoic acid and $CO_2$ to generate the starting material for C—H carboxylation. The same procedure could be used with any alkali cation and many other anions, such as sulfate $SO_4^{2-}$. The energy requirement for converting aqueous alkali chloride solutions into HCl and alkali hydroxide solutions is ~0.08 kWh per mol of alkali chloride, which would correspond to ~1 kWh per kg of FDCA. While additional energy would be required for water removal in each cycle, using highly concentrated solutions would minimize this requirement. The overall process would convert 2-furoic acid into FDCA without using any organic solvents or product distillation steps.

The ability to deprotonate unactivated C—H bonds opens the possibility of using this approach to prepare numerous high-volume and/or high-value targets. In another embodiment, $CO_3^{2-}$-promoted carboxylation described here could be used to carboxylate alkyl groups attached to aromatic rings, which have pKa values around 40.

The principle utilized in the embodiments described above could further be extended to $CO_2$ hydrogenation reactions, where $CO_2$ is combined with $H_2$ to make organic molecules. The available methods for $CO_2$ hydrogenation, which all involve transition metal catalysts, produce relatively low-value C1 compounds such as $CH_4$ and CO. In another embodiment, $CO_3^{2-}$-promoted carboxylation could be used to hydrogenate $CO_2$ to form compounds with more than one carbon. Since the pKa of $H_2$ is 35 (Kelly et al. *Phys. Chem. Chem. Phys.*, 3, 2086-2090 (2001)), the embodiments described above show that $CO_3^{2-}$ is capable of deprotonating $H_2$ at elevated temperature. $CO_3^{2-}$-promoted carboxylation of $H_2$ forms formate ($HCO_2^-$). Formate could further react to form oxalate, enabling $CO_3^{2-}$-promoted hydrogenation of $CO_2$ to oxalate. The thermochemical transformation of formate to oxalate is known (Andresen *J. Org. Chem.* 42, 2790 (1977)). In the presence of $CO_2$, $H_2$ and carbonate, oxalate could be reduced further to produce other two-carbon compounds such as acetate, ethylene, ethane, ethanol or ethylene glycol. Alternatively, formate could react with $CO_2$, $H_2$, and carbonate to produce these same products via a different intermediate.

In the specification and claims a carboxylate salt is a salt comprised of an anion that is an organic compound with a deprotonated carboxylic acid (also referred to as carboxylate) and a cation that is an alkali cation, alkaline earth cation, or other metal cation. An aromatic dicarboxylic acid is defined as a molecule with an aromatic ring that has two carboxylic acid substituents. An example would be phthalic acid (1,2-benzenedicarboxylic acid). An aromatic tricarboxylate salt is defined as a salt with a molecule with an aromatic ring that has 3 carboxylate substituents and associated cations. An example is cesium 1,3,5-benzene tricarboxylate. An Aryl acetate or aryl malonate is a molecule with an aromatic ring that has a 1-carboxyalkyl substituent or 1,1-dicarboxyalkyl substituent. An example would be cesium 3-(carboxylatomethyl)benzoate (an aryl acetate); cesium 2-(3-carboxylatophenyl)malonate (an aryl malonate).

Embodiments of Implementation

Some of the above embodiments provide a method for converting a carboxylate substrate into a dicarboxylate that has much greater value or utility than the carboxylate substrate. Some of the above embodiments provide a method of forming organic molecules from a hydrocarbon substrate without a carboxylate, such as benzene or toluene. In these embodiments, $CO_3^{2-}$ is used to depronate a carbon hydrogen bond of the substrate to form the conjugate base of the substrate. $CO_2$ is used to react with the conjugate base to add a carboxylate to the substrate. In some embodiments, a carboxylate salt that other than the substrate is added to the reaction to promote melting. In some embodiments, $Cs^+$ is the cation for the carboxylate salt(s) and $CO_3^{2-}$. In other embodiments, other cations or mixtures of cations are used including the alkali cations, alkaline earth cations, or other metal cations.

It will be obvious to those with skill in the art that conditions under which $CO_3^{2-}$ promotes a carboxylation reaction will also enable the use of bases other than $CO_3^{2-}$, such as hydroxide ($HO^-$), phosphate ($PO_4^{3-}$), or oxide ($O^{2-}$), provided as salts with alkali, alkaline earth, or other cations. In general, the use of $CO_3^{2-}$ is preferred because $CO_3^{2-}$ salts tend to be less expensive and corrosive than other bases.

Other embodiments may form organic molecules from $H_2$ and $CO_2$. In some embodiments, $CO_3^{2-}$ is used to depronate the $H_2$ to form $H^-$. $CO_2$ is used to react with the $H^-$ to form formate. The formate may be further reacted with $H_2$, $CO_3^{2-}$, and/or $CO_2$ to form compounds with more than one carbon. In some embodiments, a carboxylate salt is added to the reaction to provide a molten salt. In some embodiments, $Cs^+$ is the cation for the carboxylate salt(s) and $CO_3^{2-}$. In other embodiments, other cations or mixtures of cations are used including the alkali cations, alkaline earth cations, or other metal cations. In some embodiments, $CO_3^{2-}$ in the form of a salt with alkali, alkaline earth or other metal cations, is combined with $H_2$, $CO_2$, and $H_2O$ and heated to an elevated temperature at an elevated pressure. In some embodiments, a carboxylate salt is added to the $CO_3^{2-}$ to provide a molten component. Preferably, the mixture is heated to a temperature between 150° C. and 450° C. More preferably, the mixture is heated to a temperature between 200° C. and 400° C. Most preferably, the mixture is heated to a temperature between 250° C. and 350° C. Preferably, the elevated pressure is between 1 atm and 200 atm. More preferably, the elevated pressure is between 10 atm and 100 atm.

Other embodiments provide a method for synthesizing furan-2,5-dicarboxylate ($FDCA^{2-}$). A salt comprising furan-2-carboxylate and $CO_3^{2-}$ are mixed to form a mixture, which converts the furan-2-carboxylic acid to furan-2-carboxylate. In some embodiments, an additional carboxylate salt is added. $CO_2$ gas is provided to the mixture. The mixture may be heated to at least partially melt the furan-2-carboxylate. Both of the salts may have cesium cations. The salts may have a mixture of $Cs^+$ and $K^+$ cations. Other embodiments may only have $K^+$ cations. Other embodiments may have mixtures of cations including alkali cations, alkaline earth cations or other metal cations. Preferably, the mixture is heated to a temperature between 100° C. and 450° C. More preferably, the mixture is heated to a temperature between 200° C. and 350° C. Most preferably, the mixture is heated to a temperature between 200° C. and 300° C.

In other embodiments, aromatic tricarboxylate salts are formed by providing a mixture of an aromatic dicarboxylic acid and a $CO_3^{2-}$ salt, which converts the aromatic dicarboxylic acid to aromatic dicarboxylate. The mixture is heated under $CO_2$ gas to a temperature sufficient to at least partially melt the aromatic dicarboxylate. Preferably, the mixture is heated to a temperature between 150° C. and 450° C. More preferably, the mixture is heated to a temperature between 200° C. and 350° C. Most preferably, the mixture is heated to a temperature between 250° C. and 300° C. The aromatic dicarboxylic acid preferably is phthalic acid or is an isomer of phthalic acid, isophthalic acid, or terephthalic acid and a product is a benzene tricarboxylic acid. An additional carboxylate salt may be provided to aid melting at a lower temperature. Preferably, the aromatic dicarboxylic acid is combined with more than one equivalent of a $CO_3^{2-}$ salt to form a mixture of the aromatic dicarboxylate salt and a $CO_3^{2-}$ salt prior to heating under $CO_2$.

In other embodiments aryl acetate and aryl malonate salts are formed from a substrate with an aromatic ring substituted with an alkyl group and a carboxylic acid. A $CO_3^{2-}$ salt is provided to form a mixture, which converts the carboxylic acid to a carboxylate. The substrate and the $CO_3^{2-}$ salt are heated under $CO_2$ gas to a temperature sufficient to at least partially melt the carboxylate. Preferably, the substrate is combined with more than one-half equivalent of a $CO_3^{2-}$ salt to form a mixture of a carboxylate salt and a $CO_3^{2-}$ salt prior to heating under $CO_2$. Preferably, the mixture is heated to a temperature between 150° C. and 450° C. More preferably, the mixture is heated to a temperature between 200° C. and 350° C. Most preferably, the mixture is heated to a temperature between 250° C. and 300° C. In an embodiment, the substrate is an isomer of methylbenzoic acid. In an embodiment, an additional carboxylate salt is provided to aid melting at a lower temperature.

In other embodiments carboxylate salts are formed. An organic molecule without a carboxylate is provided. A $CO_3^{2-}$ salt is provided. A molten salt is provided. $CO_2$ gas is provided to the mixture of the organic molecule, the $CO_3^{2-}$ salt, and molten salt. The mixture is heated to maintain the molten salt. Preferably, the molten salt has $Cs^+$ cations. More preferably, the molten salt has carboxylate anions.

In the specification and claims a molten salt is a salt with a low enough melting point to be at least partially melted at a reaction temperature. Preferably, the molten salt has a melting point between 150° C. and 450° C. More preferably, the molten salt has a melting point between 200° C. and 350° C. Most preferably, the molten salt has a melting point between 250° C. and 300° C. When providing the molten salt, in some embodiments the molten salt is partially melted. In other embodiments, the molten salt may be provided in solid form and the subsequently be at least partially melted. An example of a molten salt is $Cs^+$ isobutyrate.

In the specification and claims when comparing amounts of elements or molecules, unless otherwise specified, the number of moles of the element or molecule is being compared.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for synthesizing furan-2, 5-dicarboxylate ($FDCA^{2-}$), comprising:
   providing furan-2-carboxylic acid;
   providing a $CO_3^{2-}$ salt to form a mixture, which converts the furan-2-carboxylic acid to furan-2-carboxylate;
   providing a $CO_2$ gas to the mixture;
   heating the mixture to a temperature to at least partially melt the furan-2-caboxylate.

2. The method as recited in claim 1, where the furan-2-carboxylic acid and more than one-half equivalent of $CO_3^{2-}$ salt are combined to form the mixture of furan-2-carboxylate salt and $CO_3^{2-}$ salt prior to heating under $CO_2$.

3. The method as recited in claim 1, wherein the mixture has $Cs^+$ cations.

4. The method as recited in claim 1, wherein the mixture has $K^+$ and $Cs^+$ cations.

5. The method as recited in claim 1, wherein the mixture only has $K^+$ cations and further comprising providing an additional carboxylate salt with $K^+$ cations, to aid melting at a lower temperature.

6. The method as recited in claim 1, where the temperature is between 100° C. and 450° C.

* * * * *